United States Patent [19]

Foxman

[11] Patent Number: 4,846,822
[45] Date of Patent: Jul. 11, 1989

[54] LIQUID IMPERVIOUS BARRIER MEMBER

[75] Inventor: Charles Foxman, St. Louis, Mo.

[73] Assignee: Medtex Products, Inc., St. Louis, Mo.

[21] Appl. No.: 189,335

[22] Filed: May 2, 1988

Related U.S. Application Data

[63] Continuation of Ser. No. 148,023, Jan. 25, 1988.

[51] Int. Cl.$^4$ .............................................. A61F 13/16
[52] U.S. Cl. ..................................... 604/370; 5/484;
428/91; 428/192; 428/193; 428/246; 428/247;
428/253; 428/296; 428/913; 604/366
[58] Field of Search ............... 428/110, 111, 246, 247,
428/253, 296, 91, 192, 193, 913; 5/484;
604/366, 370, 372

[56] References Cited

U.S. PATENT DOCUMENTS

| | | | |
|---|---|---|---|
| 3,282,721 | 11/1966 | Iseki | 427/245 |
| 3,600,910 | 8/1971 | Jahn et al. | 428/91 |
| 4,122,223 | 10/1978 | Civardi et al. | 428/91 |
| 4,348,445 | 9/1982 | Craig | 428/247 |
| 4,360,554 | 11/1982 | Campbell et al. | 428/91 |
| 4,595,629 | 6/1986 | Mays | 428/296 |

Primary Examiner—James J. Bell
Attorney, Agent, or Firm—Polster, Polster and Lucchesi

[57] ABSTRACT

A liquid impervious barrier member for use in a variety of medical products is disclosed as including a first outer layer of synthetic thermal plastic fabric material, an intermediate layer of thermal plastic film and a second outer layer of synthetic thermal plastic fabric material, all of the layers being heat and pressure bonded together and then cured to form the liquid impervious barrier member.

10 Claims, 2 Drawing Sheets

LIQUID IMPERVIOUS BARRIER MEMBER

This is a continuation of patent application Ser. No. 148,023 filed Jan. 25, 1988 entitled ABSORPTIVE DEVICE FOR INCONTINENT PATIENTS, now U.S. Pat. No. 4,844,965.

BACKGROUND OF THE INVENTION

This invention relates to liquid impervious barrier members for use in a variety of new and improved medical products typically used in hospitals, nursing homes and other institutions.

As disclosed in my aforementioned parent patent application Ser. No. 148,023, filed Jan. 25, 1988, now U.S. Pat. No. 4,844,965, an absorptive device for incontinent patients was disclosed as including a liquid permeable absorptive member and a liquid impervious barrier member. The liquid permeable absorptive member was disclosed as including an outer facing layer of thermal plastic material and an inner facing layer made from a material blend of thermal plastic and cellulosic fibers. The thermal plastic material outer layer was disclosed as being ultrasonically welded to the thermal plastic fibers of the blended material inner backing layer to join the layers together while allowing liquid communication through the layers. A liquid permeable absorptive member constructed in the fashion described above has numerous advantages including being quite absorptive, durable, and considerably lighter in weight than natural fabric products, providing quicker drying time at lower temperatures.

Also as disclosed in my continuation application Ser. No. 189,151 filed entitled ABSORPTIVE DEVICE WITH PROTECTIVE POCKETS, an absorptive device, such as an incontinent pad, may also be provided with protective pockets which facilitate folding, lifting and removal of the absorptive device from supporting surfaces without any contact with the contents of the absorptive device.

The liquid impervious barrier member as specifically disclosed in my aforementioned parent patent application Ser. No. 148,023 filed Jan. 25, 1988, entitled ABSORPTIVE DEVICE FOR INCONTINENT PATIENTS, now U.S. Pat. No. 4,844,965, has been used in both of the aforementioned co-pending patent applications. This liquid impervious barrier member is an important development in providing a light weight, durable, re-usable liquid impervious product that can be washed and used in excess of 200 times without deterioration. It has also been discovered that this same liquid impervious barrier member may now be used in a variety of new and improved medical product applications for the above and other advantages set forth herein. The present invention, is therefore, directed to the liquid impervious barrier member per se, as well as to the use of the liquid impervious barrier member in a variety of new and improved medical products and applications.

SUMMARY OF THE INVENTION

Among the several objects and advantages of the present invention include:

The provision of a liquid impervious barrier member for use in a variety of new and improved medical products and applications;

The provision of a liquid impervious barrier member of the type described which includes a thermal plastic film of liquid impervious material which is sandwiched between and heat and pressure bonded on opposite faces thereof to synthetic thermal plastic fabric members, the sandwich effect preventing the thermal plastic film from folding back upon and sticking to itself during the washing and drying process of laundering.

The provision of a liquid impervious barrier member of the type described which has soft patient contacting surfaces and other surfaces which inhibit slipping relative to a bed or chair as well as shifting or "bunching" of the liquid impervious barrier member during patient movement.

The provision of a liquid impervious barrier member of the type described which is considerably lighter in weight than natural fabric products to provide quicker drying time at lower temperatures, is wrinkle resistant and requires little or no ironing, is hypoallergenic, lasts twice as long as natural fabric products, is odor and mildew resistant, is bacterial and fungal resistant, meets government specifications for flame resistance, and is other wise well adapted for the purposes intended.

The foregoing and other objects and advantages of the present invention are achieved by a liquid impervious barrier member which may be used in a variety of medical products and includes a first outer layer of synthetic thermal plastic fabric material, an intermediate layer of thermal plastic film and a second outer layer of synthetic thermal plastic material, all of the layers being heat and pressure bonded together and then cured to form the liquid impervious barrier member. The liquid impervious barrier member may be formed and used in conjunction with a variety of new and improved medical products of various shapes, sizes, configurations and constructions.

The above and other objects and advantages of the present invention will become apparent from the ensuing description.

BRIEF DESCRIPTION OF THE DRAWINGS

In the drawings.

Corresponding reference characters will be used throughout the various figures of the drawing.

DESCRIPTION OF PREFERRED EMBODIMENTS

Figure 1:
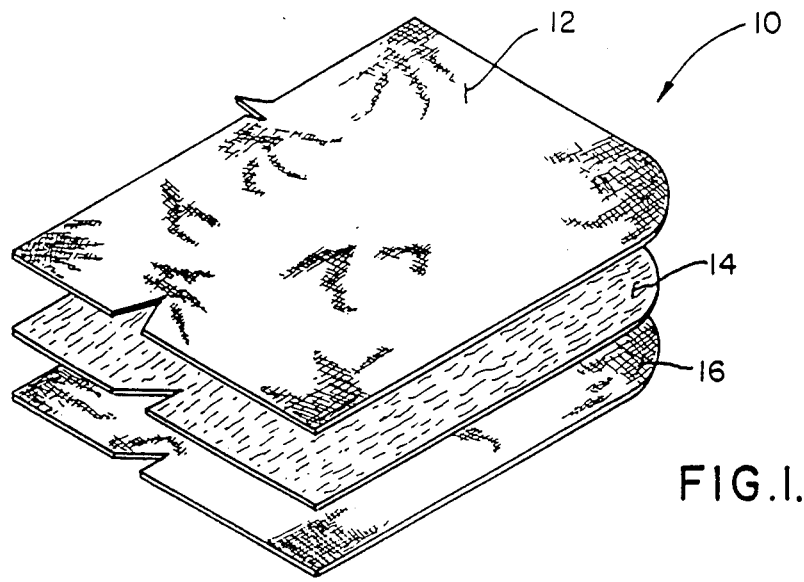
FIG. 1 is a fragmentary perspective view illustrating the three layers or membranes of the liquid impervious barrier member of the present invention, prior to being joined to one another.
Figure 2:
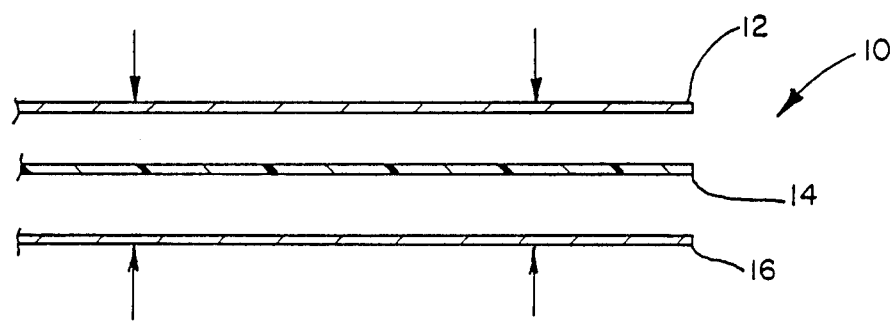
FIG. 2 is a fragmentary sectional view of the three layers or membranes of the liquid impervious barrier member of the present invention and illustrating the use of heat and pressure to bond and secure the layers or membranes to one another.
Figure 3:
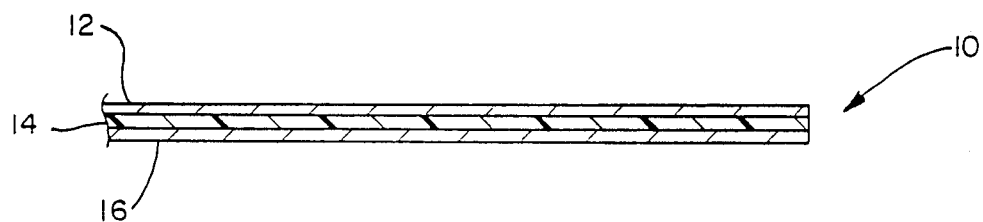
FIG. 3 is a fragmentary sectional view of the layers or membranes of the liquid impervious barrier member following the application of heat and pressure bonding and curing in order to form a joined and unitary construction for the liquid impervious barrier member.
Figure 4:
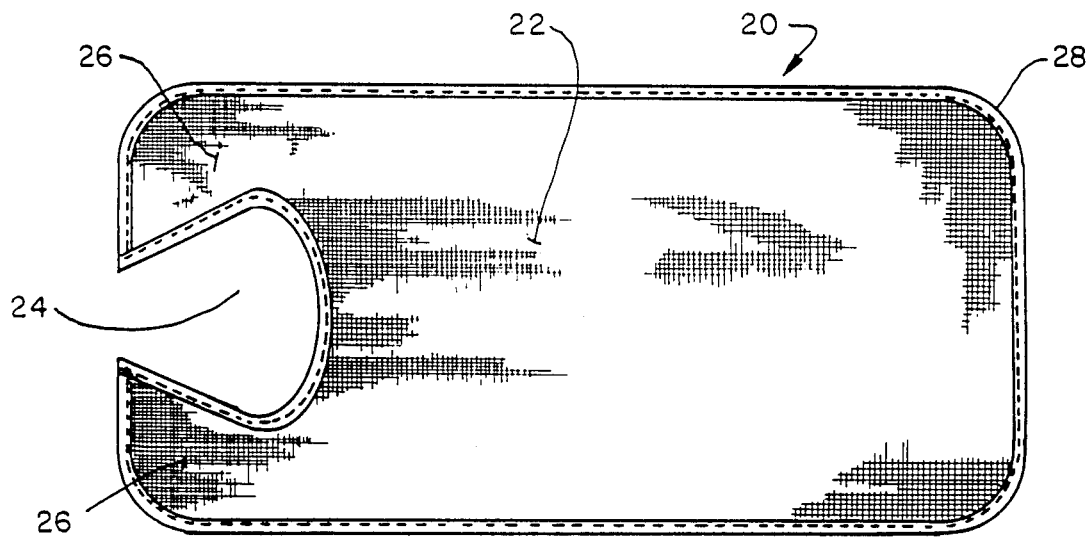
FIG. 4 is a top plan view illustrating the use of the liquid impervious barrier member in forming an adult bib together with an edge binding member also formed from the liquid impervious barrier member.
Figure 5:
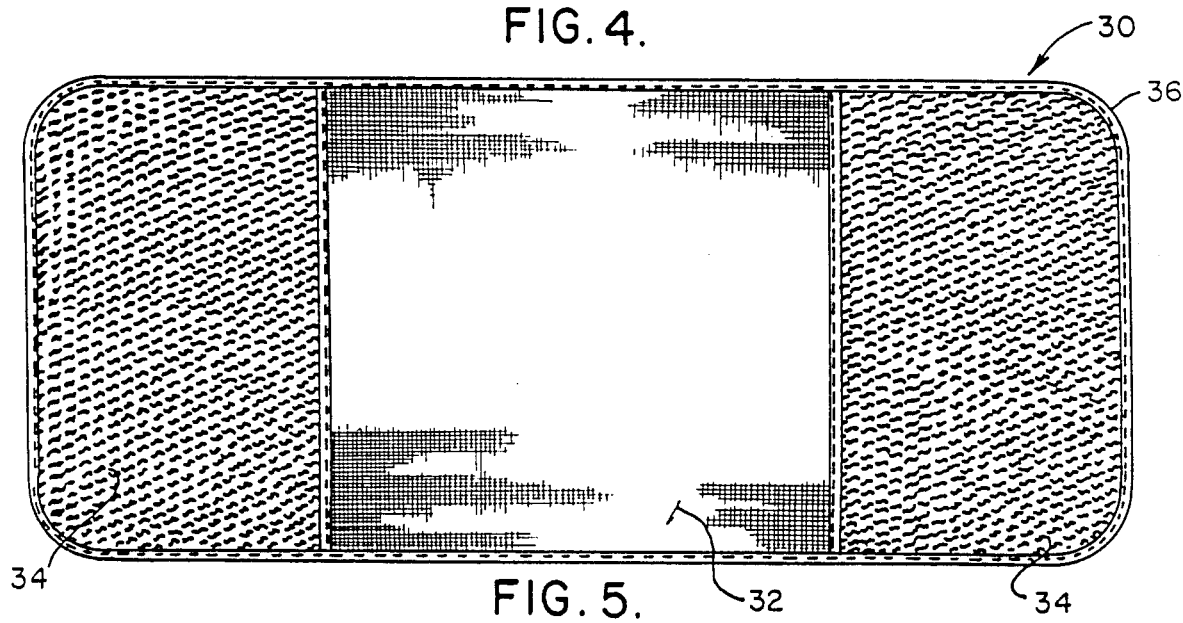
FIG. 5 is a top plan view of a draw sheet constructed from the liquid impervious barrier member and further including mesh elements attached to opposite sides of the liquid impervious barrier member.
Figure 6:
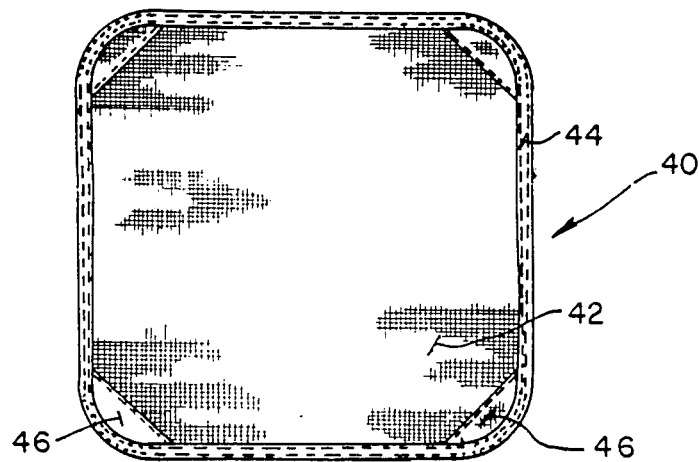
FIG. 6 is a top plan view of an incontinent pad which incorporates a liquid impervious barrier member and further is provided with protective pockets and a side or edge binding member also made from the liquid impervious barrier member material.

In the discussion that is to follow, FIGS. 1-3 of the drawings show the elements, construction and formation of the liquid impervious barrier member of the present invention, while FIGS. 4-6 show various medical products and applications using the liquid impervious barrier member of the present invention.

As shown in FIGS. 1-3 of the drawings, the liquid impervious barrier member 10 includes a first outer layer 12 of synthetic thermal plastic fabric material, preferably a woven or knitted synthetic scrim fabric having loosely woven strands or spaced interstices, to provide a relatively low cost first outer layer. An intermediate layer 14 t plastic film, preferably urethane, will adhere to the other thermal plastic layers, when heat and pressure are applied to it, as will be described below. The second outer layer 16 is also constructed from a synthetic thermal plastic fabric material which not only protects the layers and membranes, but is also preferably a napped fabric. A napped fabric for the second outer layer 16 will not allow the liquid impervious barrier member 10 to "slip or slide" on a chair or bed, while at the same time, it will maintain a neat appearance by avoiding "shifting" or "bunching" of the barrier member 10 during patient movement.

In FIG. 2 of the drawings, the arrows represent the use of heat and pressure bonding to force the three layers or membranes 12, 14, and 16 of the liquid impervious barrier member 10 into a unitary and bonded construction as shown in FIG. 3 of the drawings, following curing thereof. A liquid impervious barrier member 10, following the application of heat and pressure bonding, as well as curing, will achieve a bonding integrity so as to withstand a minimum of 200 launderings and minimum melt point of 400° F.

With a liquid impervious barrier member 10 constructed in the manner just described, the first and second outer layers of synthetic thermal plastic fabric material 12, 16 respectively, protect the sandwiched liquid impervious layer or membrane 14 of thermal plastic film from dryer heat which would cause the liquid impervious layer or membrane 14 to stick to itself, unless sandwiched between the aforementioned components. In addition, the synthetic product materials from which the liquid impervious barrier member 10 are made are considerably lighter than natural fabrics providing quicker drying time at lower temperatures. This results in obvious energy and time dollars saved during processing of the liquid impervious barrier member 10, when used by itself or in conjunction with other components to form medical products, as described below. The synthetic materials of the liquid impervious barrier member 10 are also wrinkle resistant, require little or no ironing, are hypoallergenic, last considerably longer than natural fabric products, are odor and mildew resistant, are bacterial and fungal resistant, have soil release characteristics and meet government specifications for flame resistance.

Reference is now made to FIGS. 4-6 of the drawings for examples of various types of medical products and applications which can be constructed from the liquid impervious barrier member 10 of the present invention.

In FIG. 4 of the drawings, an adult bib 20 is disclosed as including an elongated apron or body member 22 having a neck opening 24 at one end thereof with adjacent overlapping shoulder guards 26, 26 which are designed to be brought into overlapping relationship to one another and secured by any suitable fastening means (not shown). In addition to the apron body 22, the adult bib 20 may also be provided with an edge or side binding member 28 which is sewn along the outer or marginal edges of the apron body 22 providing a reinforced and durable construction. The edge or side binding member 28 is also preferably formed from a liquid impervious barrier member 10, as constructed in the manner set forth above.

FIG. 5 of the drawings shows a draw sheet medical product 30 having a center panel 32 formed from the liquid impervious barrier member material and having generally opposed mesh sections 34, 34 attached to opposite side edges of the center panel member 32. A side or edge binding member 36 may be formed from the liquid impervious barrier member 10 or some other material may be used, as desired. The typical application of the draw sheet 30 is for a hospital or nursing bed where the center panel 32 overlies that portion of the bed which would normally be subjected to wetting, with the opposed mesh sections 34, 34 being tucked under the mattress to retain the draw sheet medical product 30 into a tight conforming relationship to the bed on which it is used. The draw sheet medical product 30 is used where incontinency is not a major problem, but must nevertheless be dealt with in certain situations.

Where incontinency is a major problem, an incontinent pad 40 as shown in FIG. 6 of the drawings may be used. As disclosed in my aforementioned co-pending patent application Ser. No. 148,023 filed Jan. 25, 1988 entitled ABSORPTIVE DEVICE FOR INCONTINENT PATIENTS now U.S. Pat. No. 4,844,965 the incontinent pad 40 includes a liquid impervious barrier member 42 constructed in the manner as the liquid impervious barrier member 10 of the present invention and a side binding member 44, also preferably formed from the liquid impervious barrier member 10. In addition, protective pockets 46 for lifting, folding and removing the incontinent pad 40 from a supporting surface without contact or exposure to the nurse or attendant may be used as is disclosed in my co-pending patent application Ser. No. 189,151 filed, May 22, 1988 entitled ABSORPTIVE DEVICE WITH PROTECTIVE POCKETS. A liquid permeable absorptive member is also used in conjunction with the aforementioned components, as disclosed in my aforementioned co-pending patent applications.

From the foregoing, it will be appreciated that the liquid impervious barrier member of the present invention may be used by itself or in conjunction with a variety of new and improved medical products or components. The liquid impervious barrier member thus achieves all of the foregoing and other objects and advantages of the present invention.

As various changes could be made in the above constructions without departing from the scope of this invention, it is intended that all matter contained in the above description or shown in the accompanying drawings shall be interpreted as illustrative and not in a limiting sense.

I claim:

1. A liquid impervious barrier member for use in a variety of medical products, comprising a first outer layer of synthetic thermal plastic fabric material, an intermediate layer of thermal plastic film, and a second outer layer of synthetic thermal plastic fabric material which is also a napped fabric, all of said layers being heat and pressure bonded together to form said liquid impervious barrier member.

2. The barrier member as defined in claim 1 wherein the first outer layer s made from a knitted or woven synthetic scrim fabric, and said second outer layer is formed from a knitted or woven thermal plastic fabric.

3. The barrier member as defined in claim 2 wherein the first outer layer of knitted or woven synthetic scrim fabric has much greater spacing in the fabric yarns then those fabric yarns in the second outer layer of woven thermal plastic fabric.

4. The barrier member as defined in claim 2 wherein said intermediate layer of film is made from a material that will withstand a minimum melt point of 400° F.

5. A liquid impervious barrier member for use in a variety of medical products, comprising a first outer layer of knitted or woven synthetic scrim fabric material, an intermediate layer of thermal plastic film, and a second outer layer of woven synthetic thermal plastic fabric material, which is also a napped fabric, all of said layers being heat and pressure bonded together to form said liquid impervious barrier member.

6. The barrier member as defined in claim 5 which is formed as the main component of a medical product.

7. The barrier member as defined in claim 6 and further including an edge binding member which is also formed from the liquid impervious barrier member.

8. The barrier member as defined in claim 5 for use in conjunction with a liquid permeable absorptive member to form an incontinent pad.

9. The barrier member as defined in claim 8 and further including protective pockets also formed from the liquid impervious barrier member.

10. The barrier member as defined in claim 6 and further including other components attached to the medical product, said other components being made from materials other than said layers comprising said barrier member.

* * * * *

UNITED STATES PATENT AND TRADEMARK OFFICE
CERTIFICATE OF CORRECTION

PATENT NO. : 4,846,822

DATED : July 11, 1989

INVENTOR(S) : Charles Foxman

It is certified that error appears in the above-identified patent and that said Letters Patent is hereby corrected as shown below:

Column 1, line 7 after "4,844,965" insert -- , and patent application Serial No. 189,151 filed May 22, 1988 entitled ABSORPTIVE DEVICE WITH PROTECTIVE POCKETS, now U.S. Patent No. _____. --;

Column 1, line 34 after "filed" insert -- May 22, 1988 --;

Column 2, line 9 shifting should be -- "shifting" --;

Column 3, line 16 "t" should be --of thermal--.

Column 5, line 5, "layer s" should be --layer is--.

Signed and Sealed this

Eighth Day of May, 1990

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,846,822
DATED : July 11, 1989
INVENTOR(S) : Charles Foxman

It is certified that error appears in the above-identified patent and that said Letters Patent is hereby corrected as shown below:

On the title page:

Assignee: Medtex Products, Inc. should be -- Medpat, Inc.--

Signed and Sealed this

Seventeenth Day of July, 1990

Attest:

HARRY F. MANBECK, JR.

*Attesting Officer*   *Commissioner of Patents and Trademarks*